(12) United States Patent
Leonhartsberger et al.

(10) Patent No.: US 7,371,551 B1
(45) Date of Patent: ***May 13, 2008

(54) FEEDBACK-RESISTANT HOMOSERINE TRANSSUCCINYLASES

(75) Inventors: Susanne Leonhartsberger, München (DE); Kerstin Pfeiffer, München (DE); Christoph Winterhalter, Pöcking (DE); Brigitte Bauer, München (DE)

(73) Assignee: Consortium für elektrochemische Industrie GmbH, München (DE)

( * ) Notice: Subject to any disclaimer, the term of this patent is extended or adjusted under 35 U.S.C. 154(b) by 215 days.

This patent is subject to a terminal disclaimer.

(21) Appl. No.: 10/530,843

(22) PCT Filed: Oct. 2, 2003

(86) PCT No.: PCT/EP03/10978

§ 371 (c)(1),
(2), (4) Date: Apr. 8, 2005

(87) PCT Pub. No.: WO2004/035617

PCT Pub. Date: Apr. 29, 2004

(30) Foreign Application Priority Data

Oct. 11, 2002 (DE) ............................... 102 47 437

(51) Int. Cl.
*C12N 9/10* (2006.01)
*C12N 1/20* (2006.01)
*C12N 15/00* (2006.01)
*C07H 21/04* (2006.01)

(52) U.S. Cl. ............... 435/193; 435/252.3; 435/320.1; 536/23.2

(58) Field of Classification Search ................ 435/193, 435/252.3, 320.1; 536/23.2
See application file for complete search history.

(56) References Cited

U.S. PATENT DOCUMENTS

| 5,120,837 A | 6/1992 | Fotheringham et al. |
| 5,698,418 A | 12/1997 | Brunner et al. |
| 2002/0106800 A1 | 8/2002 | Liaw et al. |

FOREIGN PATENT DOCUMENTS

| EP | 0 745 671 A2 | 12/1996 |
| JP | 2000-139471 A | 5/2000 |

OTHER PUBLICATIONS

Thomson Derwent corresponding to JP 2000-139471 A.
Morinaga et al., Agric. Biol. Chem., vol. 46, No. 1, 1982, pp. 57-63.
Bourhy et al., Journal of Bacteriology, vol. 179, No. 13, Jul. 1997, pp. 4396-4398.
Duclos, B. et al.,"Nucleotide sequence of the metA gene encoding homoserine trans-succinylase in *Escherichia coli*." Nucleic Acids Research, vol. 17, No. 7, 1989, p. 2856.
Lawrence et al., Dept. of Genetics, vol. 58, Apr. 1968, pp. 473-492.
Kiedich et al., "The Enzymic Synthesis of L-Cysteine in *Escherichia coli* and *Salmonella typhimurium*," J. Biol. Chem., 1966, vol. 241, No. 21, pp. 4955-4965.
Lee et al., "Multimetabolite Control of a Biosynthetic Pathway of Sequential Metabolities," J. Biol. Chem., vol. 24, No. 22, 1966, pp. 5479-5480.
Shiozaki et al., Agric. Biol. Chem., vol. 53, No. 12. 1989, pp. 3269-3274.
Schlenk et al., "The Formation of S-Adenosylmethionine in yeast," J. Biol. Chem., 1957, pp. 1037-1050.
Greene et al., "Biosynthesis of Methionine," ASM Press, Washington 1996, *Escherichia coli* and *Salmonella typhimurium*, Second Edition, pp. 542-560.
Hornung et al., Proc. Natl. Acad. Sci. USA, vol. 96, Mar. 1999, pp. 4192-4197.
Born et al., Biochemistry, Oct. 1999, vol. 38, No. 43, pp. 14416-14423 as abstract.
Chattopadhyay et al. "Control of Methionine Biosynthesis in *Escherichia coli* K 12: a closer study with analoque-resistant mutants," Journal of General Microbiology, 1991, vol. 137, pp. 685-691.
Chattopadhyay et al., Control of methionine biosynthesis in *Escherichia coli* K12: a closer study with analogue-resistant mutants, Journal of General Microbiology, 1991, pp. 685-691, vol. 137.

*Primary Examiner*—Tekchand Saidha
(74) *Attorney, Agent, or Firm*—Collard & Roe, P.C.

(57) ABSTRACT

The invention concerns a homoserine transsuccinylase having at least one mutation compared to a wild-type homoserine transsuccinylase and reduced sensitivity towards a L-methionine or SAM, compared to the wild-type enzyme. The latter comprises an amino acid sequence including a partial AspGlyXaaXaaXaaThrGlyAlaPro sequence between position 90 and position 115 and a partial TyrGlnXaaThrPro sequence between position 285 and position 310, position 1 of the amino acid sequence corresponding to the initial methionine. The invention is characterized in that the mutation is a substitution of the aspartate in the partial AspGlyXaaXaaXaaThrGlyAlaPro sequence, or a substitution of the tyrosine in the partial TyrGlnXaaThrPro sequence.

8 Claims, 1 Drawing Sheet

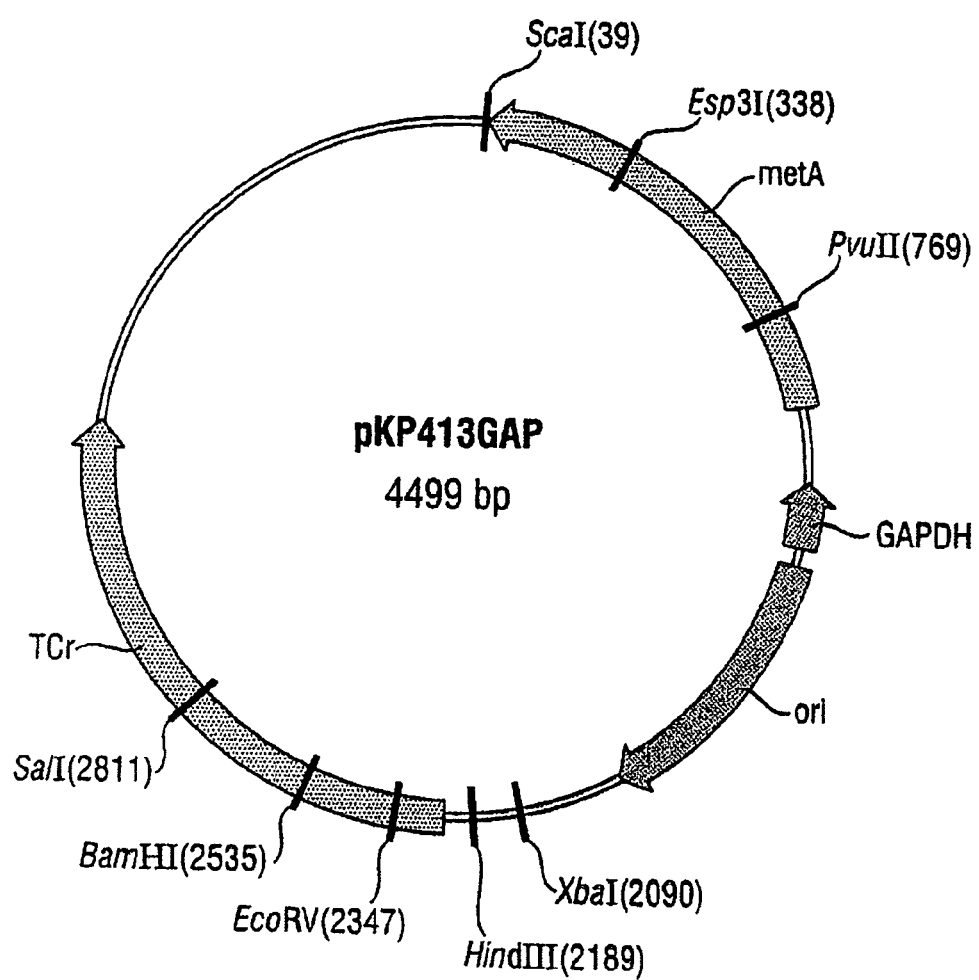
Fig. 1: pKP413GAP

FEEDBACK-RESISTANT HOMOSERINE TRANSSUCCINYLASES

CROSS REFERENCE TO RELATED APPLICATIONS

Applicants claim priority under 35 U.S.C. §119 of German Application No. 102 47 437.0 filed Oct. 11, 2002. Applicants also claim priority under 35 U.S.C. §365 of PCT/EP2003/010978 filed Oct. 2, 2003. The international application under PCT article 21(2) was not published in English.

BACKGROUND OF THE INVENTION

The present invention relates to feedback-resistant homoserine transsuccinylases, to microorganism strains containing these enzymes and to their use for preparing L-methionine or S-adenosylmethionine.

Methionine is an amino acid which is essential for humans and many animals. It is, in particular, produced for the feedstuff market and added to animal feed as the racemate. It is synthesized chemically from acrolein and methanethiol by way of 3-(methylthio)-propionaldehyde, which is converted, with hydrogen cyanide, ammonia and carbon dioxide, into D,L-methionine by way of an hydantoin. The racemate can be resolved enzymically.

S-Adenosylmethionine (SAM) is the most important methyl group donor in metabolism and, in the pharmaceutical field, is used in the treatment of depressions, diseases of the liver and arthritis. Methods which have been described for preparing SAM include, in particular, culturing yeasts (Schlenk F. and DePalma R. E., J. Biol. Chem. 1037-1050 (1957), Shiozaki S. et al., Agric. Biol. Chem. 53, 3269-3274 (1989)) in the presence of the precursor L-methionine and chromatographically purifying after autolysis.

The microbial synthesis of methionine has been investigated particularly intensively in the bacterium *E. coli* (Greene, R. C., Biosynthesis of Methionine in: Neidhardt F. C., *Escherichia coli* and *Salmonella typhimurium*, Cellular and molecular biology, Second Edition, ASM Press, Washington D.C. (1996), pages 542-560 and the references contained therein). It consists of a number of enzyme-catalyzed reactions and is strictly regulated. The first steps in the synthesis, from aspartate to homoserine, proceed in parallel with the formation of the amino acids threonine, leucine, isoleucine and valine. The first step which is specific for the synthesis of methionine is the formation of O-succinylhomoserine from succinyl-CoA and homoserine with the elimination of coenzyme A. This reaction is catalyzed by the enzyme homoserine succinyltransferase (homoserine O-transsuccinylase, MetA, EC 2.3.1.46). SAM is synthesized from L-methionine and ATP in one step.

The activity of homoserine transsuccinylase is inhibited in the presence of L-methionine and/or SAM (Lee L.-W. et al., J. Biol. Chem. 241, 5479-5480 (1966)). While this end product inhibition on the one hand prevents an excessive, energy-consuming synthesis of methionine and SAM in the bacterium, it also, on the other hand, stands in the way of the microbial production of these two substances on an industrial scale. The gene encoding homoserine transsuccinylase consists of 930 base pairs (including the stop codon), while the protein encoded by this gene consists of 309 amino acids. The structure of homoserine transsuccinylase has not thus far been elucidated and it is therefore not possible, either, to identify the amino acids which are involved in an end product inhibition.

A known method of increasing the synthesis of metabolic end products is that of using modified enzymes whose activity can no longer be inhibited by the end product of their metabolic pathway (feedback-resistant mutants). Thus, for example, feedback-resistant mutants of 3-deoxy-D-arabinoheptulonic acid 7-phosphate synthase have been prepared for increasing the synthesis of L-tryptophan and L-phenylalanine (EP0745671A2) and feedback-resistant mutants of chorismate mutase/prephenate dehydratase have been generated for increasing the production of phenylalanine (U.S. Pat. No. 5,120,837).

The *E. coli* enzyme homoserine transsuccinylase has recently been modified, by mutating the DNA sequence encoding it, such that the activity of the resulting proteins is much less readily inhibited in the presence of 1 mM L-methionine or 1 mM SAM (JP2000139471A). The mutation involved the following amino acid replacements: arginine at position 27 was replaced with cysteine, isoleucine at position 296 was replaced with serine and proline at position 298 was replaced with leucine. The modified homoserine transsuccinylases exhibited residual activities of between 44 and 89% in the presence of 1 mM L-methionine and of between 10 and 73% in the presence of 1 mM SAM. Bacterial strains which contain these modified proteins produce L-methionine to an increased extent. However, in the absence of L-methionine and SAM, these modified homoserine transsuccinylases have an activity which is much less than that seen in the wild type. It is desirable to have available as many variants of homoserine transsuccinylase, which differ in the degree of their activity and in the degree to which they can be inhibited by L-methionine and/or SAM, as possible since the microbial biosynthesis of L-methionine and SAM is highly complex in regard to its course and regulation and, in addition, is interlinked, in a multifaceted manner, with a variety of other metabolic pathways in the cell. It is therefore not possible to make any prediction in advance as to which variant can achieve which effect on the growth of a microorganism strain, on the balance of its vital metabolic processes and on the production of L-methionine and SAM.

SUMMARY OF THE INVENTION

The object of the present invention is to make available a broad spectrum of novel variants of homoserine transsuccinylase (MetA protein) which exhibit a feedback resistance in regard to L-methionine and SAM which is increased as compared with that of the wild-type (WT) enzyme.

This object is achieved by means of a homoserine transsuccinylase which possesses at least one mutation as compared with a homoserine transsuccinylase wild-type enzyme and exhibits a reduced sensitivity towards L-methionine or SAM as compared with the wild-type enzyme, with the wild-type enzyme possessing an amino acid sequence which comprises a constituent sequence AspGlyXaaXaaXaaThrGlyAlaPro between positions 90 and 115 and a constituent sequence TyrGlnXaaThrPro between positions 285 and 310, with position 1 of the amino acid sequence being the starting methionine, characterized in that the mutation is an amino acid replacement of the aspartate in the constituent sequence AspGlyXaaXaaXaaThrGlyAlaPro or an amino acid replacement of the tyrosine in the constituent sequence TyrGlnXaaThrPro.

A comparison of homoserine transsuccinylases in various microorganisms shows that the Asp in the constituent sequence AspGlyXaaXaaXaaThrGlyAlaPro and the Tyr in the constituent sequence TyrGlnXaaThrPro are conserved. In the *E. coli* MetA protein, the sequence region AspGlyXaaXaaXaaThrGlyAlaPro containing the conserved aspartate Asp is located between positions 101 and 109 of SEQ ID No. 2. In other MetA proteins, it is located in the region between positions 90 and 115. In the *E. coli* MetA protein, the sequence region TyrGlnXaaThrPro containing the conserved tyrosine Tyr is located between positions 294 and 298 of SEQ ID No. 2. In other MetA proteins, it is located in the region between positions 285 and 310. Xaa denotes any arbitrary natural amino acid.

The spatial structure of homoserine transsuccinylase has not thus far been elucidated. It is not possible, therefore, to assign different functions, such as enzymic activity and inhibitability by L-methionine and/or SAM, to particular amino acids. Since the folding of proteins is an extremely complex process, it is not possible to draw conclusions as to spatial structure from the primary sequence of proteins and it is not uncommon for amino acids which are widely separated from each other in the primary sequence to be located in immediate proximity in the folded protein, and vice versa. It has been found, surprisingly, that the amino acid replacements according to the invention at position 101 or 294 of the protein lead to a reduction in the feedback-inhibitability both with regard to L-methionine and with regard to SAM.

A homoserine transsuccinylase according to the invention exhibits a resistance (that is an increase in Ki) toward the inhibitors SAM and/or L-methionine which is superior to that of the wild-type enzyme. Preferably, it exhibits a resistance toward methionine and/or SAM which is at least 2-fold that of the wild type. Particularly preferably, a homoserine transsuccinylase according to the invention has a resistance toward methionine and/or SAM which is 10-fold that of the wild type, particularly preferably a resistance which is increased 50-fold, very particularly preferably a resistance which is higher than that of the MetA mutants specified in JP2000139471A.

Particularly preferably, the protein sequence of a homoserine transsuccinylase according to the invention contains one of the mutations listed in table 1 or a combination of the listed mutations.

A homoserine transsuccinylase according to the invention can be obtained, for example, by expressing a DNA sequence which encodes a homoserine transsuccinylase according to the invention.

The present invention consequently also relates to a DNA sequence which encodes a homoserine transsuccinylase according to the invention.

Such a DNA sequence can be obtained by mutating a base in one or more codons of a MetA gene, characterized in that at least one mutation is present in the codon for the conserved aspartate which is located in position 101 in the *E. coli* wild-type enzyme or in the codon for the conserved tyrosine which is located in position 294 in the *E. coli* wild-type enzyme, with codon 1 beginning with the first base of sequence SEQ ID No. 1.

A DNA sequence according to the invention is a MetA gene in which the codon for the aspartate Asp in the sequence AspGlyXaaXaaXaaThrGlyAlaPro, with this sequence being located between positions 90 and 115 in the MetA protein, and/or the codon for the conserved tyrosine Tyr in the sequence TyrGlnXaaThrPro, with this sequence being located between positions 285 and 310, is/are modified.

In that which follows, a DNA sequence according to the invention is designated a feedback-resistant MetA allele.

Within the context of the present invention, those genes which, in an analysis using the BESTFIT algorithm (GCG Wisconsin Package, Genetics Computer Group (GCG) Madison, Wis.), exhibit a sequence identity of more than 50% with the *E. coli* WT metA gene are also to be understood as being metA alleles. In precisely the same way, proteins which have a sequence identity of more than 50% with the *E. coli* wild-type homoserine transsuccinylase (BESTFIT algorithm, GCG Wisconsin Package, Genetics Computer Group (GCG) Madison, Wis.), and which possess homoserine transsuccinylase activity, are to be understood as being homoserine transsuccinylases.

A metA allele according to the invention preferably contains one of the mutations listed in table 1, column 2 or 4, or a combination of the listed mutations.

MetA alleles according to the invention can be prepared, for example, by means of nonspecific mutagenesis or targeted mutagenesis, from starting material which is described below. Nonspecific mutations within said DNA region can be produced, for example, by means of chemical agents (e.g. 1-methyl-3-nitro-1-nitrosoguanidine, ethyl methanesulfonic acid, and the like) and/or by means of physical methods and/or by means of PCR reactions carried out under defined conditions, and/or by means of amplifying the DNA in mutator strains (e.g. XL1 red). Methods for introducing mutations at specific positions within a DNA fragment are known. Another possibility of generating feedback-resistant metA alleles consists in combining different, feedback resistance-inducing mutations to give rise to multiple mutants possessing new properties.

The DNA of a wild-type metA gene is preferably used as the starting material for the mutagenesis. The metA gene to be mutated can be encoded chromosomally or extrachromosomally. The abovementioned mutagenesis methods are used to modify one or more nucleotides of the DNA sequence such that the protein which is now encoded by the gene possesses a mutation of the conserved aspartate, which is located in position 101 in the *E. coli* wild-type enzyme, or a mutation of the conserved tyrosine, which is located at position 294 in the *E. coli* wild-type enzyme, with position 1 being the starting methionine from SEQ ID No. 2.

The techniques which have been described can be used to introduce one or more mutations in said DNA region in any arbitrary metA gene. These mutations result in the encoded homoserine transsuccinylase possessing an amino acid sequence which leads to feedback resistance in relation to SAM and/or L-methionine.

After the mutagenesis, which has, for example, been carried out as described, the mutants possessing the desired phenotype are selected, for example by determining the extent of the sensitivity of the mutated homoserine transsuccinylases to L-methionine and/or SAM.

Any method which enables the activity of the enzyme to be determined in the presence of L-methionine or SAM can be used for determining the sensitivity of the homoserine transsuccinylase to L-methionine and/or SAM. For example, the homoserine transsuccinylase activity can be determined by following the method described by Kredich and Tomkins for determining the activity of serine acetyltransferases (Kredich N. M. and Tomkins G. M., J. Biol. Chem. 241, 4955-4965 (1966)). The enzyme activity is measured in an assay sample which contains homoserine and succinyl-CoA. The reaction is started by adding enzyme and monitored in a spectrophotometer by way of the decrease in the extinction at 232 nm which results from cleavage of the thioester bond in the succinyl-coenzyme A. The described test is suitable for determining the sensitivity of the homoserine transsuccinylases to methionine. The inhibition of homoserine transsuccinylase activity is tested in the presence of different concentrations of L-methionine in the reaction mixture. The catalytic activity of the different homoserine transsuccinylases is determined in the presence and absence of L-methionine, with these data being used to calculate the inhibition constant Ki, which describes the concentration of inhibitor at which the activity is only 50% of that which can be measured in the absence of the inhibitor.

In order to determine the sensitivity of the activity of the different homoserine transsuccinylases to SAM, it is possible, for example, to carry out an activity test as described in Lee L. W. et al., J. Biol. Chem. 241, 5479-5480 (1966). In this method, the enzyme extract is incubated with homoserine and succinyl-CoA. After various times, a part of the test assay sample is stopped by adding it to a mixture of ethanol, water, and 5,5'-dithiobis(2-nitrobenzoic acid). The absorption is determined photometrically at 412 nm. The described test is suitable, for example, for determining the sensitivity of the homoserine transsuccinylases to SAM. The inhibition of the homoserine transsuccinylase activity is tested in the presence of different concentrations of SAM in the reaction mixture. The catalytic activity of the different homoserine trans-succinylases is determined in the presence and absence of SAM and the inhibition constant Ki is calculated from these data.

Preference is as a rule given to a homoserine transsuccinylase which has a reduced sensitivity to L-methionine and/or SAM while at the same time possessing a catalytic activity which is unaltered. For other purposes, it may be desirable for the L-methionine and/or SAM sensitivity and the catalytic activity to be reduced simultaneously.

The invention also relates to microorganism strains which contain feedback-resistant metA alleles according to the invention. These microorganism strains are characterized by the fact that they possess a L-methionine metabolism or SAM metabolism which is at least deregulated by a feedback-resistant metA allele. Since this metabolism proceeds by the same route, which is known per se, in all microorganisms, and the techniques to be used for producing the strains according to the invention are well-known, for example from standard textbooks, and applicable to all microorganisms, strains according to the invention can be prepared from any arbitrary microorganisms. Bacteria are preferred and suitable for producing a strain according to the invention. Gram-negative bacteria, in particular E. coli, are particularly preferably suitable.

The invention furthermore relates to the preparation of L-methionine or SAM by culturing microorganisms according to the invention and also to the use of microorganisms according to the invention for preparing products which contain methionine (such as methionine-containing peptides) or which are derived, in the metabolism of the microorganisms, from L-methionine or SAM (such as polyamines, lipoic acid, biotin or quinones). In addition, microorganisms according to the invention which produce SAM in greater quantities than does the wild type can be used for preparing products which are formed by transferring the methyl group from SAM.

In order to express the modified homoserine transsuccinylase enzyme, the feedback-resistant metA alleles are transformed into a host strain using customary methods.

A feedback-resistant metA allele can be expressed under the control of its own promoter, which is located upstream of the metA gene, or by using other suitable promoter systems which are known to the skilled person. In this connection, the corresponding gene can be present, under the control of such a promoter, either in one or more copies on the chromosome of the host organism or on a vector, preferably a plasmid. The invention therefore also relates to a plasmid, characterized in that it contains a feedback-resistant metA allele according to the invention together with a promoter.

For the cloning, it is possible to use vectors which already contain genetic elements (e.g. constitutive or regulable promoters, terminators) which enable the gene encoding a homoserine transsuccinylase to be expressed either continuously or in a controlled, inducible manner. In addition, other regulatory elements, such as ribosomal binding sites and termination sequences, and also sequences which encode selective markers and/or reporter genes, are present on an expression vector. The expression of these selection markers facilitates identification of transformants. Suitable selection markers are genes which, for example, encode resistance to ampicillin, tetracycline, chloramphenicol, kanamycin and other antibiotics. If the metA allele according to the invention is to be replicated extrachromosomally, the plasmid vector should preferably contain an origin of replication. Particular preference is given to plasmid vectors such as the E. coli vectors pACYC184, pUC18, pBR322 and pSC101 and their derivatives. Examples of suitable inducible promoters are the lac, tac, trc, lambda PL, ara and tet promoters or sequences which are derived therefrom. The constitutive expression of a GAPDH promoter is preferred. In a particularly preferred embodiment of the present invention, the genes encoding the homoserine transsuccinylase are under the control of the GAPDH promoter in a plasmid which is derived from pACYC184. The strategies for integrating genes into the chromosome are prior art.

A suitable host strain is transformed with an expression vector which contains the transcription unit which encodes a L-methionine-insensitive and/or SAM-insensitive homoserine transsuccinylase. Strains which contain L-methionine-sensitive and/or SAM-sensitive proteins, such as bacteria, are used as host strains.

The host strain which is preferably used is an E. coli wild-type strain or a strain in which the endogenous metA gene has been inactivated, such as E. coli strain DL41, CGSC strain collection No. 7177. These strains are complemented with a metA gene according to the invention. Additional measures can be used to increase the ability of a strain according to the invention to produce L-methionine or SAM microbially. For example, it is possible, for this purpose, to use strains in which the metJ gene, which encodes a repressor of the methionine metabolism genes, is no longer expressed (JP2000139471A).

L-Methionine or SAM is preferably produced by culturing a microorganism strain according to the invention. For this, the microorganism strain is cultured, for example, in a fermenter in a nutrient medium which contains a suitable carbon source and a suitable energy source as well as other additives.

The substances, such as L-methionine or SAM, which are formed during the fermentation can subsequently be purified.

The following examples serve to provide further clarification of the invention. All the molecular biological methods employed, such as polymerase chain reaction, isolation and purification of DNA, modification of DNA with restriction enzymes, Klenow fragment and ligase, transformation, etc., were carried out in the manner known to the skilled person, in the manner described in the literature or in the manner recommended by the respective manufacturers.

BRIEF DESCRIPTION OF THE DRAWING

Other objects and features of the present invention will become apparent from the following detailed description considered in connection with the accompanying drawing. It is to be understood, however, that the drawing is designed as an illustration only and not as a definition of the limits of the invention.

FIG. 1 shows a plasmid pKP413GAP produced according to the invention.

DETAILED DESCRIPTION OF THE PREFERRED EMBODIMENT

The invention will now be described with reference to the following Examples

Example 1

Using Undirected Mutagenesis of the metA Structural Gene to Generate Feedback-Resistant Homoserine Transsuccinylases The *E. coli* metA gene was amplified by the polymerase chain reaction using the 5'-end-phosphorylated oligonucleotides metAfw, having the sequence 5'-GATCCCATGGCTCCTTTTAGTCATTCTTAT-3' (SEQ ID No. 3), and metArev, having the sequence 5'-GATCGAGCTCAGTACTATTAATC-CAGCGTTGGATTC-3' (SEQ ID No. 4), as primers and chromosomal DNA from *E. coli* strain W3110 (ATCC 27325) as the substrate. The product, which was 1.1 kb in length, was isolated electrophoretically and purified using a QIAquick gel extraction kit (Qiagen). After that, T4 DNA ligase was used to insert it into plasmid pBR322 (MBI Fermentas) which had been treated with the restriction enzyme EcoRI and the Klenow fragment (Roche). The resulting plasmid, i.e. pKP438, was used for the mutagenesis.

Plasmid pKP438 was introduced, by means of transformation, into the *E. coli* strain XL1-Red (Stratagene) and mutations were inserted in plasmid pKP438 by means of culturing the strain in accordance with the manufacturer's instructions. The mutagenesis was effected in the presence of critical concentrations of methionine analogs, as described in Lawrence D. A. and Smith D. A., Genetics 58: 473-492 (1968). This procedure selects mutants which overproduce methionine. Most of these mutants can be attributed to modified homoserine transsuccinylases encoded on plasmid pKP438.

The plasmids from two mutants were isolated and the DNA sequences of the metA genes were determined. It was found that the two genes in each case contained one base replacement as compared with the wild type, with these base replacements resulting in one amino acid being changed in the homoserine transsuccinylases which were in each case encoded. metA in pBR1 contains an A, instead of the G which is present in the wild-type gene, as base 301, resulting in asparagine instead of aspartate being incorporated at position 101 in the encoded protein. pBR3 contains a G, instead of the A which is present in the wild-type gene, as base 881, resulting in cysteine being incorporated instead of tyrosine at position 294 in the encoded protein.

Example 2

Using Specific Base Replacements in the metA Structural Gene to Generate Feedback-Resistant Homoserine Transsuccinylases metA alleles which encode homoserine transsuccinylases which are feedback-resistant in regard to L-methionine and/or SAM, due to base replacements and accompanying amino acid changes at positions 101 and, respectively, 294 (see Examples 3 and 4) were prepared in Example 1. Site-specific mutagenesis was therefore used to construct genes which encoded homoserine trans-succinylases in which either the amino acid aspartate at position 101 or the amino acid tyrosine at position 294 is replaced with a variety of other amino acids and which, as a result, exhibit altered properties with regard to the inhibition of their activity by L-methionine and SAM.

The plasmid pACYC184-LH, which is derived from pACYC184 and which is deposited in the Deutsche Sammlung für Mikroorganismen und Zellkulturen [German collection of microorganisms and cell cultures] in Brunswick under the number DSM 10172, was used as the basal plasmid for constructing the plasmids according to the invention. The sequence of the GAPDH promoter, and also an NdeI cleavage site upstream thereof, were inserted into this plasmid using the following procedure: the GAPDH promoter was amplified by the polymerase chain reaction using the rules known to the skilled person, with the oligonucleotides GAPDHfw, having the sequence 5'-GTCGACGCGTGAGGCGAGTCAGTCGCGTAATGC-3' (SEQ ID No. 5), and GAPDHrevII, having the sequence 5'-GACCTTAATTAAGATCTCATATGTTC-CACCAGCTATTTGTTA-3' (SEQ ID No. 6), serving as primers and chromosomal DNA from *E. coli* strain W3110 (ATCC 27325) serving as substrate. The product was isolated electrophoretically, purified using a QIAquick gel extraction kit (Qiagen) and treated with the restriction enzymes MluI and PacI in accordance with the manufacturer's instructions. After that, it was inserted, using T4 ligase, into a pACYC184-LH vector which had been treated with the same enzymes, resulting in the formation of plasmid pKP290.

The *E. coli* metA gene is amplified by means of the polymerase chain reaction using the oligonucleotides metAfw2, having the sequence 5'-CATGGCTCCTTTTAGTCATTCTTATAT-TCTAACGTAG-3' (SEQ ID No. 7), and metArev2, having the sequence 5'-ACGCGTATGCATCCAGAGCTCAGTAC-TATTAATCCAGCGTTGGATTC-3' (SEQ ID No. 8), as primers and chromosomal DNA from *E. coli* strain W3110 (ATCC 27325) as the substrate. The product, which was 1.1 kb in length, was separated electrophoretically and purified using a QIAquick gel extraction kit (Qiagen). After that, the product was ligated into vector pKP290, which had been prepared in the following manner: treatment with restriction enzyme NdeI, Klenow enzyme, restriction enzyme BglII and mung bean nuclease (Roche). The resulting plasmid, i.e. pKP413GAP, is depicted in FIG. 1 and is deposited in the Deutsche Sammlung für Mikroorganismen und Zellkulturen [German collection of microorganisms and cell cultures] in Brunswick under the number DSM 15221. It contains the *E. coli* metA gene under the control of the GAPDH promoter and serves as the starting plasmid for preparing the feedback-resistant metA alleles.

Plasmid pKP413GAP was subjected to site-specific directed mutagenesis in regard to codon 294 of the metA structural gene. For this, an inverse polymerase chain reaction using Pfu polymerase (Promega) was carried out in accordance with the rules known to the skilled person. The primers used were the 5'-end-phosphorylated oligonucleotides metAmutfw1, having the sequence 5'-NNNCAGATCACGCCATACGATCTAC-3' (SEQ ID No. 9), with a 1:1:1:1 mixture of A, T, C and G being employed for N in the synthesis, and metAmutrev1, having the sequence 5'-GACGTAATAGTTGAGCCAGTTGG-3' (SEQ ID No. 10).

The product, which was about 4.3 kb in size, was isolated electrophoretically and purified using a QIAquick gel extraction kit (Qiagen) in accordance with the manufacturer's instructions. After that, T4 DNA ligase was used, in accordance with the manufacturer's instructions, to perform an intramolecular ligation. E. coli cells of the strain DH5a were transformed using the CaCl$_2$ method in the manner known to the skilled person. The transformation mixture was spread on LB-tetracycline agar plates (10 g of tryptone/l, 5 g of yeast extract/l, 10 g of NaCl/l, 15 g of agar/l, 15 mg of tetracycline/l) and the latter were incubated at 37° C. overnight. Following plasmid isolation using a QIAprep spin miniprep kit (Qiagen), the desired transformants were identified by means of a restriction analysis. The region between the Esp3I and ScaI cleavage sites, which contains codon 294 of the metA structural gene, was sequenced and isolated and inserted into a pKP413GAP plasmid which had been treated with the same enzymes, using methods known to the skilled person.

While the procedure for the directed mutagenesis in regard to codon 101 was analogous, the primers employed for the polymerase chain reaction were the oligonucleotides metAmutfw2, having the sequence 5'-NNNGGTTTGATTGTAACTGGTGCG-3' (SEQ ID No. 11), with a 1:1:1:1 mixture of A, T, C and G being used for N in the synthesis, and metAmutrev2, having the sequence 5'-AAAGTTCTGATCCTGAATATC-3' (SEQ ID No. 12).

The plasmids having a position at codon 101 which was changed as compared with the wild-type metA were sequenced in the region between the Esp3I and PvuII cleavage sites, isolated and inserted into a pKP413GAP plasmid which had been treated with the same enzymes.

The plasmids which have been constructed in this way contain the complete metA gene possessing a sequence at codon 294 or, respectively, 101 which is in each case altered as compared with the wild-type sequence, thereby making it possible to use them to produce different homoserine transsuccinylase variants (Table 1).

TABLE 1

Starting plasmid and plasmids which contain metA variants possessing an altered codon 101 or 294, respectively.

| Plasmid | Codon 101 | Amino acid 101 | Codon 294 | Amino acid 294 |
|---|---|---|---|---|
| pKP413GAP | GAC | Asp | TAC | Tyr |
| pKP446 | GAC | Asp | TGC | Cys |
| pSLmetA*L | GAC | Asp | CTC | Leu |
| pSLmetA*A | GAC | Asp | GCC | Ala |
| pSLmetA*P | GAC | Asp | CCT | Pro |
| pSLmetA*Q | GAC | Asp | CAG | Gln |
| pSLmetA*K | GAC | Asp | AAG | Lys |
| pSLmetA*0 | GAC | Asp | —*) | —**) |
| pSLmetAN | AAC | Asn | TAC | Tyr |
| pSLmetAH | CAC | His | TAC | Tyr |
| pSLmetAC | TGT | Cys | TAC | Tyr |
| pSLmetAS | AGC | Ser | TAC | Tyr |
| pSLmetAY | TAC | Tyr | TAC | Tyr |
| pSLmetAA | GCG | Ala | TAC | Tyr |
| pSLmetAI | ATC | Ile | TAC | Tyr |

*)Codon 294 is missing in the metA sequence
**)Amino acid 294 is deleted

Example 3

Activity of the Homoserine Transsuccinylase Mutants, and Feedback Resistance in Regard to L-Methionine The activity, and the influence of L-methionine on the activity, of the different homoserine transsuccinylases were determined by means of an enzyme test using cell extracts in which the respective proteins had been produced. For this, the corresponding plasmids, encoding altered homoserine transsuccinylases, were introduced, by transformation, into the E. coli strain W3110 (ATCC 27325) using methods known to the skilled person. The transformation mixture was spread on LB-tetracycline agar plates (10 g of tryptone/l, 5 g of yeast extract/l, 5 g of NaCl/l, 15 g of agar/l and 15 mg of tetracycline/l) and incubated at 37° C. overnight. The resulting transformants were grown in SM1 medium (for 1 l of medium: CaCl$_2 \times$2H$_2$O, 0.0147 g, MgSO$_4 \times$7H$_2$O, 0.3 g, Na$_2$MoO$_4 \times$2H$_2$O, 0.15 mg, H$_3$BO$_3$, 2.5 mg, CoCl$_2 \times$6H$_2$O, 0.7 mg, CuSO$_4 \times$5H$_2$O, 0.25 mg, MnCl$_2 \times$4H$_2$O, 1.6 mg, ZnSO$_4 \times$7H$_2$O, 0.3 mg, KH$_2$PO$_4$, 3.0 g, K$_2$HPO$_4$, 12.0 g, (NH$_4$)$_2$SO$_4$, 5 g, NaCl, 0.6 g, FeSO$_4 \times$7H$_2$O, 0.002 g, Na$_3$-citrate$\times$2H$_2$O, 1 g, glucose, 5 g, tryptone, 1 g, yeast extract, 0.5 g), centrifuged down at an absorption of approx. 0.8 at 600 nm, washed in 50 mM Tris pH 7.5, and centrifuged down once again. The cells were resuspended in 50 mM Tris/Cl, pH 7.5, 2 mM dithiothreitol, 0.5 mM phenylmethylsulfonyl fluoride and disrupted in a French press. The supernatant from a further centrifugation was used as the enzyme extract in the test. The enzyme activity was determined, in a mixture containing 50 mM Tris/Cl, pH 7.6, 1 mM homoserine and 0.1 mM succinyl-CoA, by photometrically quantifying, by means of the decrease in the extinction at 232 nm, the coenzyme A formed in the reaction, following the method described by Kredich and Tomkins for determining the activity of serine acetyltransferases (Kredich N. M. and Tomkins G. M., J. Biol. Chem. 241, 4955-4965 (1966)). The effect of added L-methionine on the activity was determined and the inhibitability was quantified as a Ki value. The Ki which is determined is the concentration of L-methionine at which the activity of the homoserine transsuccinylase is only 50% of its activity in the absence of L-methionine.

All the homoserine transsuccinylase mutants exhibit a feedback resistance in regard to L-methionine which is elevated as compared with that of the wild type. Table 2 summarises the results.

TABLE 2

Activities of the WT enzyme and the homoserine transsuccinylase mutants, and feedback resistances in regard to L-methionine.

| Plasmid | Activity (U/mg) | Activity (%)* in the presence of 1 mM L-methionine | L-Methionine Ki (mM) |
|---|---|---|---|
| pKP413GAP | 0.155 | 2 | 0.05 |
| pKP446 | 0.133 | 96 | 11 |
| pSLmetA*L | 0.070 | 89 | 6.5 |
| pSLmetA*A | 0.063 | 94 | 7.5 |
| pSLmetA*P | 0.020 | 91 | 6 |
| pSLmetA*Q | 0.065 | 95 | 11 |
| pSLmetA*K | 0.048 | 92 | 12.5 |
| pSLmetA*0 | 0.085 | 98 | 14.5 |
| pSLmetAN | 0.050 | 86 | 8 |
| pSLmetAH | 0.045 | 90 | 12 |
| pSLmetAC | 0.084 | 92 | 5 |
| pSLmetAS | 0.027 | 89 | 7.5 |
| pSLmetAY | 0.094 | 93 | 10 |
| pSLmetAA | 0.031 | 96 | 6 |
| pSLmetAI | 0.107 | 95 | 9.5 |

*Activity in the absence of L-methionine corresponds to 100%.

Example 4

Feedback Resistance of the Homoserine Transsuccinylases in Regard to SAM

The influence of SAM on the activities of the different homoserine transsuccinylases was determined by quantifying the activity in the presence of different concentrations of SAM (Cl salt, Sigma). The cell extracts were grown and prepared as described in Example 3. The activity test was carried out as described in Lee L. W. et al., J. Biol. Chem. 241, 5479-5480 (1966), with the enzyme extract being incubated with 50 mM potassium phosphate buffer, pH 7.5, 3 mM homoserine and 0.3 mM succinyl-CoA. After various times, 100 µl volumes of test mixture were stopped by adding them in each case to a mixture of 400 µl of ethanol, 400 µl of water and 100 µl of 10 mM 5,5'-dithiobis(2-nitrobenzoic acid). After the resulting mixture had been incubated at room temperature for 5 minutes, the absorption was determined photometrically at 412 nm. After the protein concentration had been determined, the enzyme activity was calculated using the extinction coefficient. The Ki was determined as a measure of the ability of SAM to inhibit the activity.

TABLE 3

Activities of the homoserine transsuccinylase mutants, and feedback resistances in regard to SAM.

| Plasmid | Activity (U/mg) | Activity (%)* in the presence of 1 mM SAM | SAM Ki (mM) |
|---|---|---|---|
| pKP413GAP | 0.62 | 0.5 | 0.2 |
| pKP446 | 0.49 | 92 | 10 |
| pSLmetA*L | 0.29 | 80 | 7 |
| pSLmetA*A | 0.26 | 95 | 10 |
| pSLmetA*P | 0.15 | 98 | 18 |
| pSLmetA*Q | 0.21 | 87 | 6 |
| pSLmetA*K | 0.14 | 90 | 5 |
| pSLmetA*0 | 0.33 | 96 | 10 |
| pSLmetAN | 0.30 | 91 | 13 |
| pSLmetAH | 0.27 | 93 | 16 |
| pSLmetAC | 0.51 | 91 | 7 |
| pSLmetAS | 0.15 | 89 | 10 |
| pSLmetAY | 0.61 | 95 | 14 |
| pSLmetAA | 0.20 | 90 | 8 |
| pSLmetAI | 0.68 | 93 | 12 |

*Activity in the absence of SAM corresponds to 100%.

The invention claimed is:

1. A homoserine transsuccinylase which possesses at least one mutation as compared with a homoserine transsuccinylase wild-type enzyme and exhibits a reduced sensitivity toward L-methionine or SAM as compared with the wild-type enzyme, with the wild-type enzyme possessing an amino acid sequence of SEQ ID NO: 2 which comprises a constituent sequence AspGlyXaaXaaXaaThrGlyAlaPro between positions 90 and 115 and a constituent sequence TyrGlnXaaThrPro between positions 285 and 310, with position 1 of the amino acid sequence being the starting methionine, wherein the mutation is an amino acid replacement of the aspartate in the constituent sequence AspGlyXaaXaaXaaThrGlyAlaPro or an amino acid replacement of the tyrosine in the constituent sequence TyrGlnXaaThrPro.

2. A homoserine transsuccinylase as claimed in claim 1, wherein it exhibits a resistance toward SAM or L-methionine which is increased (increased Ki) at least 2-fold as compared with that of the wild type.

3. A homoserine transsuccinylase as claimed in claim 1, wherein it contains a mutation selected from the group consisting of Asp101Asn, Asp101His, Asp101Cys, Asp101Ser, Asp101Tyr, Asp101Ala, Asp101Ile, Tyr294Cys, Tyr294Leu, Tyr294 Ala, Tyr294Pro, Tyr294Gln, Gyr294Lys, and a mutation wherein Tyr294 is deleted.

4. An isolated nucleic acid or an isolated metA allele which encodes a homoserine transsuccinylase as claimed in claim 1.

5. A plasmid transformed with an isolated nucleic acid encoding homoserine transsuccinylase as claimed in claim 4 together with a promoter.

6. An isolated microbial host cell, wherein it contains a feedback-resistant metA allele as claimed in claim 4.

7. An isolated microbial host cell as claimed in claim 6, wherein it is a Gram-negative bacterial strain, preferably *E. coli*.

8. A method for preparing L-methionine or SAM by culturing an isolated microbial host cell as claimed in claim 6.

* * * * *

SEQUENCE LISTING

```
<160> NUMBER OF SEQ ID NOS: 12

<210> SEQ ID NO 1
<211> LENGTH: 930
<212> TYPE: DNA
<213> ORGANISM: Escherichia coli
<220> FEATURE:
<221> NAME/KEY: CDS
<222> LOCATION: (1)..(930)
<300> PUBLICATION INFORMATION:
<301> AUTHORS: Blattner, F. R.
<302> TITLE: The complete genome sequence of Escherichia coli K-12.
<303> JOURNAL: Science
<304> VOLUME: 277
<305> ISSUE: 5331
<306> PAGES: 1453-1474
<307> DATE: 1997

<400> SEQUENCE: 1 atg ccg att cgt gtg ccg gac gag cta ccc gcc gtc aat ttc ttg cgt      48
Met Pro Ile Arg Val Pro Asp Glu Leu Pro Ala Val Asn Phe Leu Arg
 1               5                  10                  15
```

```
gaa gaa aac gtc ttt gtg atg aca act tct cgt gcg tct ggt cag gaa      96
Glu Glu Asn Val Phe Val Met Thr Thr Ser Arg Ala Ser Gly Gln Glu
             20                  25                  30 att cgt cca ctt aag gtt ctg atc ctt aac ctg atg ccg aag aag att     144
Ile Arg Pro Leu Lys Val Leu Ile Leu Asn Leu Met Pro Lys Lys Ile
         35                  40                  45 gaa act gaa aat cag ttt ctg cgc ctg ctt tca aac tca cct ttg cag     192
Glu Thr Glu Asn Gln Phe Leu Arg Leu Leu Ser Asn Ser Pro Leu Gln
     50                  55                  60 gtc gat att cag ctg ttg cgc atc gat tcc cgt gaa tcg cgc aac acg     240
Val Asp Ile Gln Leu Leu Arg Ile Asp Ser Arg Glu Ser Arg Asn Thr
 65                  70                  75                  80 ccc gca gag cat ctg aac aac ttc tac tgt aac ttt gaa gat att cag     288
Pro Ala Glu His Leu Asn Asn Phe Tyr Cys Asn Phe Glu Asp Ile Gln
                 85                  90                  95 gat cag aac ttt gac ggt ttg att gta act ggt gcg ccg ctg ggc ctg     336
Asp Gln Asn Phe Asp Gly Leu Ile Val Thr Gly Ala Pro Leu Gly Leu
            100                 105                 110 gtg gag ttt aat gat gtc gct tac tgg ccg cag atc aaa cag gtg ctg     384
Val Glu Phe Asn Asp Val Ala Tyr Trp Pro Gln Ile Lys Gln Val Leu
        115                 120                 125 gag tgg tcg aaa gat cac gtc acc tcg acg ctg ttt gtc tgc tgg gcg     432
Glu Trp Ser Lys Asp His Val Thr Ser Thr Leu Phe Val Cys Trp Ala
    130                 135                 140 gta cag gcc gcg ctc aat atc ctc tac ggc att cct aag caa act cgc     480
Val Gln Ala Ala Leu Asn Ile Leu Tyr Gly Ile Pro Lys Gln Thr Arg
145                 150                 155                 160 acc gaa aaa ctc tct ggc gtt tac gag cat cat att ctc cat cct cat     528
Thr Glu Lys Leu Ser Gly Val Tyr Glu His His Ile Leu His Pro His
                165                 170                 175 gcg ctt ctg acg cgt ggc ttt gat gat tca ttc ctg gca ccg cat tcg     576
Ala Leu Leu Thr Arg Gly Phe Asp Asp Ser Phe Leu Ala Pro His Ser
            180                 185                 190 cgc tat gct gac ttt ccg gca gcg ttg att cgt gat tac acc gat ctg     624
Arg Tyr Ala Asp Phe Pro Ala Ala Leu Ile Arg Asp Tyr Thr Asp Leu
        195                 200                 205 gaa att ctg gca gag acg gaa gaa ggg gat gca tat ctg ttt gcc agt     672
Glu Ile Leu Ala Glu Thr Glu Glu Gly Asp Ala Tyr Leu Phe Ala Ser
    210                 215                 220 aaa gat aag cgc att gcc ttt gtg acg ggc cat ccc gaa tat gat gcg     720
Lys Asp Lys Arg Ile Ala Phe Val Thr Gly His Pro Glu Tyr Asp Ala
225                 230                 235                 240 caa acg ctg gcg cag gaa ttt ttc cgc gat gtg gaa gcc gga cta gac     768
Gln Thr Leu Ala Gln Glu Phe Phe Arg Asp Val Glu Ala Gly Leu Asp
                245                 250                 255 ccg gat gta ccg tat aac tat ttc ccg cac aat gat ccg caa aat aca     816
Pro Asp Val Pro Tyr Asn Tyr Phe Pro His Asn Asp Pro Gln Asn Thr
            260                 265                 270 ccg cga gcg agc tgg cgt agt cac ggt aat tta ctg ttt acc aac tgg     864
Pro Arg Ala Ser Trp Arg Ser His Gly Asn Leu Leu Phe Thr Asn Trp
        275                 280                 285 ctc aac tat tac gtc tac cag atc acg cca tac gat cta cgg cac atg     912
Leu Asn Tyr Tyr Val Tyr Gln Ile Thr Pro Tyr Asp Leu Arg His Met
    290                 295                 300 aat cca acg ctg gat taa                                              930
Asn Pro Thr Leu Asp
305

<210> SEQ ID NO 2
<211> LENGTH: 309
```

```
<212> TYPE: PRT
<213> ORGANISM: Escherichia coli

<400> SEQUENCE: 2

Met Pro Ile Arg Val Pro Asp Glu Leu Pro Ala Val Asn Phe Leu Arg
 1               5                  10                  15

Glu Glu Asn Val Phe Val Met Thr Thr Ser Arg Ala Ser Gly Gln Glu
            20                  25                  30

Ile Arg Pro Leu Lys Val Leu Ile Leu Asn Leu Met Pro Lys Lys Ile
        35                  40                  45

Glu Thr Glu Asn Gln Phe Leu Arg Leu Leu Ser Asn Ser Pro Leu Gln
    50                  55                  60

Val Asp Ile Gln Leu Leu Arg Ile Asp Ser Arg Glu Ser Arg Asn Thr
65                  70                  75                  80

Pro Ala Glu His Leu Asn Asn Phe Tyr Cys Asn Phe Glu Asp Ile Gln
                85                  90                  95

Asp Gln Asn Phe Asp Gly Leu Ile Val Thr Gly Ala Pro Leu Gly Leu
            100                 105                 110

Val Glu Phe Asn Asp Val Ala Tyr Trp Pro Gln Ile Lys Gln Val Leu
        115                 120                 125

Glu Trp Ser Lys Asp His Val Thr Ser Thr Leu Phe Val Cys Trp Ala
    130                 135                 140

Val Gln Ala Ala Leu Asn Ile Leu Tyr Gly Ile Pro Lys Gln Thr Arg
145                 150                 155                 160

Thr Glu Lys Leu Ser Gly Val Tyr Glu His His Ile Leu His Pro His
                165                 170                 175

Ala Leu Leu Thr Arg Gly Phe Asp Asp Ser Phe Leu Ala Pro His Ser
            180                 185                 190

Arg Tyr Ala Asp Phe Pro Ala Ala Leu Ile Arg Asp Tyr Thr Asp Leu
        195                 200                 205

Glu Ile Leu Ala Glu Thr Glu Glu Gly Asp Ala Tyr Leu Phe Ala Ser
    210                 215                 220

Lys Asp Lys Arg Ile Ala Phe Val Thr Gly His Pro Glu Tyr Asp Ala
225                 230                 235                 240

Gln Thr Leu Ala Gln Glu Phe Phe Arg Asp Val Glu Ala Gly Leu Asp
                245                 250                 255

Pro Asp Val Pro Tyr Asn Tyr Phe Pro His Asn Asp Pro Gln Asn Thr
            260                 265                 270

Pro Arg Ala Ser Trp Arg Ser His Gly Asn Leu Leu Phe Thr Asn Trp
        275                 280                 285

Leu Asn Tyr Tyr Val Tyr Gln Ile Thr Pro Tyr Asp Leu Arg His Met
    290                 295                 300

Asn Pro Thr Leu Asp
305

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide metAfw

<400> SEQUENCE: 3
gatcccatgg ctccttttag tcattcttat                                    30
```

```
<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence:
      Oligonucleotide metArev

<400> SEQUENCE: 4
gatcgagctc agtactatta atccagcgtt ggattc                                 36

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence:
      Oligonucleotide GAPDHfw

<400> SEQUENCE: 5
gtcgacgcgt gaggcgagtc agtcgcgtaa tgc                                    33

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence:
      Oligonucleotide GAPDHrevII

<400> SEQUENCE: 6
gaccttaatt aagatctcat atgttccacc agctatttgt ta                          42

<210> SEQ ID NO 7
<211> LENGTH: 37
<212> TYPE: DNA
<213> ORGANISM: Artificial Sequence
<220> FEATURE:
<223> OTHER INFORMATION: Description of Artificial Sequence:
      Oligonucleotide metAfw2

<400> SEQUENCE: 7
catggctcct tttagtcatt cttatattct aacgtag                                37

<210> SEQ ID NO 8
<211> LENGTH: 47
<212> TYPE: DNA
<213> ORGANISM: Artificial Sequence
<220> FEATURE:
<223> OTHER INFORMATION: Description of Artificial Sequence:
      Oligonucleotide metArev2

<400> SEQUENCE: 8
acgcgtatgc atccagagct cagtactatt aatccagcgt tggattc                     47

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide metAmutfw1; n=1:1:1:1 mixture of A,T,C and G.

<400> SEQUENCE: 9
nnncagatca cgccatacga tctac                                             25

<210> SEQ ID NO 10
```

```
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide metAmutrev1

<400> SEQUENCE: 10
gacgtaatag ttgagccagt tgg                                           23

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide metAmutfw2; N is a 1:1:1:1: mixture of A, T, C and
      G

<400> SEQUENCE: 11
nnnggtttga ttgtaactgg tgcg                                          24

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide metAmutrev2

<400> SEQUENCE: 12
aaagttctga tcctgaatat c                                             21
```